(12) United States Patent
Schwartz et al.

(10) Patent No.: US 9,506,904 B2
(45) Date of Patent: Nov. 29, 2016

(54) DEVICE FOR MEASURING THE AMOUNT OF FREE FLUID IN A COLLOID IN A HORIZONTAL POSITION

(71) Applicant: HALLIBURTON ENERGY SERVICES, INC., Houston, TX (US)

(72) Inventors: Michael W. Schwartz, Rock Springs, WY (US); Dennis Gray, Duncan, OK (US); Benjamin J. Iverson, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 464 days.

(21) Appl. No.: 13/856,321

(22) Filed: Apr. 3, 2013

(65) Prior Publication Data
US 2014/0298895 A1 Oct. 9, 2014

(51) Int. Cl.
*G01N 19/00* (2006.01)
*G01N 33/38* (2006.01)

(52) U.S. Cl.
CPC .................................. *G01N 33/383* (2013.01)

(58) Field of Classification Search
USPC ........................................................ 73/427
See application file for complete search history.

(56) References Cited

U.S. PATENT DOCUMENTS

| | | | | |
|---|---|---|---|---|
| 1,399,394 A | * | 12/1921 | Mond | B01L 3/508 422/940 |
| 2,931,230 A | * | 4/1960 | Lowery | G01F 19/00 215/227 |
| 3,047,195 A | * | 7/1962 | Richmond | B65D 47/121 222/189.01 |
| 4,109,530 A | * | 8/1978 | Kim | G01F 19/00 600/584 |
| 4,747,304 A | | 5/1988 | King | |
| 6,000,470 A | | 12/1999 | Skinner et al. | |
| 2003/0049857 A1 | | 3/2003 | Chan | |
| 2005/0138991 A1 | | 6/2005 | Wallevik et al. | |
| 2011/0167901 A1 | | 7/2011 | Jamison et al. | |

\* cited by examiner

*Primary Examiner* — Paul West
*Assistant Examiner* — Mark A Shabman
(74) *Attorney, Agent, or Firm* — McGuireWoods LLP (57) ABSTRACT

A device for testing the amount of free fluid in a colloid comprises: a first container, wherein the first container has a central axis that spans the length of the first container, wherein the length of the first container is greater than the width and height of the first container, and wherein the central axis of the first container is oriented in a substantially horizontal position during the testing. Methods of using the device include: optically determining the height of free fluid in the container after the period of time has elapsed and using a formula to determine the volume of the free fluid; or removing a plug from a plug tube that is operationally connected to the container; and draining the free fluid from the container into a measurement device.

15 Claims, 6 Drawing Sheets

DEVICE FOR MEASURING THE AMOUNT OF FREE FLUID IN A COLLOID IN A HORIZONTAL POSITION

TECHNICAL FIELD

An apparatus and method of use for testing the amount of free fluid in a cement composition are provided. The apparatus and methods allow the cement composition to be tested in a horizontal position. This allows for the determination of the amount of free fluid in a cement composition in a simulated horizontal wellbore.

SUMMARY

According to an embodiment, a device for testing the amount of free fluid in a colloid comprises: a first container, wherein the first container has a central axis that spans the length of the first container, wherein the length of the first container is greater than the width and height of the first container, and wherein the central axis of the first container is oriented in a substantially horizontal position during the testing.

According to another embodiment, a method for testing the amount of free fluid in a colloid comprises: filling a container with a known amount of the colloid; maintaining the container with the colloid for a period of time in a substantially horizontal position; optically determining the height of free fluid in the container after the period of time has elapsed; and using a formula to determine the volume of the free fluid.

According to a further embodiment, a method for testing the amount of free fluid in a colloid comprises: filling a container with a known amount of the colloid; maintaining the container with the colloid for a period of time in a substantially horizontal position; removing a plug from a plug tube that is operationally connected to the container after the period of time has elapsed, wherein an end of the plug tube is positioned in at least a portion of the free fluid; and draining the free fluid from the container into a measurement device.

BRIEF DESCRIPTION OF THE FIGURE

The features and advantages of certain embodiments will be more readily appreciated when considered in conjunction with the accompanying figures. The figures are not to be construed as limiting any of the preferred embodiments.

DETAILED DESCRIPTION

As used herein, the words "comprise," "have," "include," and all grammatical variations thereof are each intended to have an open, non-limiting meaning that does not exclude additional elements or steps.

As used herein, a "fluid" is a substance having a continuous phase that tends to flow and to conform to the outline of its container when the substance is tested at a temperature of 71° F. (22° C.) and a pressure of one atmosphere "atm" (0.1 megapascals "MPa"). A fluid can be a liquid or gas. A homogenous fluid has only one phase, whereas a heterogeneous fluid has more than one distinct phase. A colloid is an example of a heterogeneous fluid. A colloid can be: a slurry, which includes a continuous liquid phase and undissolved solid particles as the dispersed phase; an emulsion, which includes a continuous liquid phase and at least one dispersed phase of immiscible liquid droplets; a foam, which includes a continuous liquid phase and a gas as the dispersed phase; or a mist, which includes a gas as the continuous phase and liquid droplets as the dispersed phase. As used herein, the term "emulsion" means a colloid in which an aqueous liquid is the continuous phase and a hydrocarbon liquid is the dispersed phase. As used herein, the term "invert emulsion" means a colloid in which a hydrocarbon liquid is the continuous phase and an aqueous liquid is the dispersed phase. Any of the phases of an emulsion or invert emulsion can contain dissolved materials and/or undissolved solids. Moreover, it is to be understood there can be more than one dispersed phase of a colloid, but only one external phase. For example, there can be a continuous phase, which is adjacent to a first dispersed phase, and the first dispersed phase can be adjacent to a second dispersed phase. A slurry containing a liquid continuous phase, a first dispersed phase of insoluble particles, and a second dispersed phase of a gas is an example of a multi-dispersed phase colloid.

As used herein, a "cement composition" is a mixture of at least cement and water. A cement composition can include additives. As used herein, the term "cement" means an initially dry substance that, in the presence of water, acts as a binder to bind other materials together. An example of cement is Portland cement. A cement composition is generally a slurry in which the water is the continuous phase of the slurry and the cement (and any other insoluble particles) is the dispersed phase. The continuous phase of a cement composition can include dissolved solids.

Oil and gas hydrocarbons are naturally occurring in some subterranean formations. In the oil and gas industry, a subterranean formation containing oil or gas is referred to as a reservoir. A reservoir may be located under land or off shore. Reservoirs are typically located in the range of a few hundred feet (shallow reservoirs) to a few tens of thousands of feet (ultra-deep reservoirs). In order to produce oil or gas, a wellbore is drilled into a reservoir or adjacent to a reservoir. The oil, gas, or water produced from the wellbore is called a reservoir fluid.

A well can include, without limitation, an oil, gas, or water production well, an injection well, or a geothermal well. As used herein, a "well" includes at least one wellbore. The wellbore is drilled into a subterranean formation. The subterranean formation can be a part of a reservoir or adjacent to a reservoir. A wellbore can include vertical, inclined, and horizontal portions, and it can be straight, curved, or branched. As used herein, the term "wellbore" includes any cased, and any uncased, open-hole portion of the wellbore. A near-wellbore region is the subterranean material and rock of the subterranean formation surrounding the wellbore. As used herein, a "well" also includes the near-wellbore region. The near-wellbore region is generally considered the region within approximately 100 feet radially of the wellbore. As used herein, "into a well" means and includes into any portion of the well, including into the wellbore or into the near-wellbore region via the wellbore.

A portion of a wellbore may be an open hole or cased hole. In an open-hole wellbore portion, a tubing string may be placed into the wellbore. The tubing string allows fluids to be introduced into or flowed from a remote portion of the wellbore. In a cased-hole wellbore portion, a casing is placed into the wellbore, which can also contain a tubing string. A wellbore can contain an annulus. Examples of an annulus include, but are not limited to: the space between the wellbore and the outside of a tubing string in an open-hole wellbore; the space between the wellbore and the outside of a casing in a cased-hole wellbore; and the space between the inside of a casing and the outside of a tubing string in a cased-hole wellbore.

During well completion, it is common to introduce a cement composition into an annulus in a wellbore. For example, in a cased-hole wellbore, a cement composition can be placed into and allowed to set in an annulus between the wellbore and the casing in order to stabilize and secure the casing in the wellbore. By cementing the casing in the wellbore, fluids are prevented from flowing into the annulus. Consequently, oil or gas can be produced in a controlled manner by directing the flow of oil or gas through the casing and into the wellhead. Cement compositions can also be used in primary or secondary cementing operations, well-plugging, squeeze cementing, or gravel packing operations.

There are many different formulations for a cement composition. Changing the concentration of ingredients, the ingredients themselves, or the processing of the mixture can result in cement compositions that have different properties. Furthermore, the cement may set in different manners based upon different environmental conditions, e.g., temperature, humidity, pressure, the wellbore composition, and formation properties.

One particular problem with cement compositions is the presence of free fluid in the composition. Free fluid can be a result of a non-homogenous cement composition. For example, free fluid can arise from having too much liquid, such as water, or migrating gas in the cement composition or insufficient suspending agents in the composition whereby the solids can settle out of the composition. Free fluid can comprise excess water containing dissolved solids and/or other solids from the cement composition that can float to the top of the cement composition. Free fluid typically is observed during cement hydration, but technically can occur at any time after the cement and water have been mixed together. Since the free fluid is less dense than the remaining cement composition, the free fluid tends to rise to the top of the cement composition in a container or wellbore. One of the major problems with the formation of free fluid in a cement composition is that poor or incomplete cement bonding to a tubular in a wellbore, such as a casing, can occur. This can cause a weak area in the wellbore annulus where the cement composition did not bond with the tubular.

Consequently, it is advantageous to test a cement composition to determine if the specific composition and concentration of ingredients will result in an undesirable amount of free fluid. The testing may also be conducted to simulate one or more environmental conditions that the cement composition would be subjected to during a cementing operation.

There are known testing procedures for determining the amount of free fluid in a cement composition. For example, one typical testing procedure is set forth in API Recommended Practice 10B-2, section 15 entitled "Well-simulation slurry stability tests."

Section 15.4 tests the amount of free fluid when heat is applied to the cement composition and Section 15.5 tests the free fluid at ambient temperature. However, there are currently no tests capable of simulating the free fluid formation in a horizontal wellbore. For example, the apparatus used for testing in Section 15 is an open-ended cylinder that the cement composition is placed into and remains in a vertical position during testing. The cylinder cannot be tilted to an angle greater than approximately 55° past vertical (i.e., wherein 0° is an axis perpendicular to the Earth's surface and 90° is a plane of the Earth's surface) without the cement composition spilling out of the open end of the cylinder. Thus, there is a need for being able to test the amount of free fluid that may form in a cement composition when simulating a horizontal wellbore. As used herein, the term "horizontal wellbore" means the portion of a wellbore that is not perpendicular to the earth's surface. For example, horizontal wellbore portions include, but are not limited to, highly deviated, tangents that are highly deviated, horizontal sections, or portions that turn up-dip (i.e., the wellbore goes from a downward substantially vertical orientation to horizontal and then to an upward substantially vertical orientation). It is to be understood that a wellbore can include both vertical sections and horizontal sections. The vertical section would be the portion of the wellbore that is substantially perpendicular to the earth's surface. It is also to be understood that a horizontal wellbore can include angled, curved, and/or straight sections.

It has been discovered that a testing apparatus can be used to test the amount of free fluid formed in a cement composition for simulating a horizontal wellbore. The apparatus can be positioned in a substantially horizontal position during the testing such that the actual amount of free fluid formed in a horizontal wellbore can be determined.

As used herein, the amount of free fluid in a colloid is performed as follows: at least one container is filled with a known volume of the colloid. The container is sealed so that the colloid cannot independently exit the container. The container preferably has a length to inner diameter ratio between 6:1 and 8:1. The container is placed in a substantially horizontal position and tested at a specified temperature and pressure. For example, the testing can be conducted at ambient temperature and pressure (i.e., 71° F. and 1 atm) or at a temperature and/or pressure above ambient temperature and pressure. The container is allowed to remain static for a minimum of 2 hours. The amount of free fluid formed during the testing is then determined using a variety of methods described in detail below. As used herein, the phrase "substantially horizontal" means in a position substantially parallel with respect to the surface of the Earth.

According to an embodiment, a device for testing the amount of free fluid in a colloid comprises: a first container, wherein the first container has a central axis that spans the length of the first container, wherein the length of the first container is greater than the width and height of the first container, and wherein the central axis of the first container is oriented in a substantially horizontal position during the testing.

Any discussion of the embodiments regarding the device for testing or any component thereof (e.g., the first container) is intended to apply to all of the apparatus and method embodiments. Any discussion of a particular component of an embodiment (e.g., a first container) is meant to include the singular form of the component and the plural form of the component, without the need to continually refer to the component in both the singular and plural form throughout. For example, if a discussion involves "the container 20," it is to be understood that the discussion pertains to a first or second container (singular) and two or more containers, e.g., the first and second containers 20*a* and 20*b* (plural).

One embodiment is a device for testing the amount of free fluid 11 in a colloid 10, shown in FIG. 1. The colloid can be a slurry, an emulsion, an invert emulsion, or a foam. The free fluid can comprise a liquid, and can be a solution, a lower density emulsion/invert emulsion, a foam, a mist, or a slurry containing lower density insoluble particulates and a lower density liquid, wherein reference to density is with respect to the density of the colloid. Preferably, the colloid is a slurry and the free fluid is water. The water of the free fluid can include dissolved substances or insoluble lower density particulates. According to an embodiment, the slurry is a cement composition. The cement composition can comprise cement, water, and optionally other ingredients, such as additives. The additives can be any additives that would replicate the actual composition of the cement slurry to be used in a cementing operation.

Figure 7:
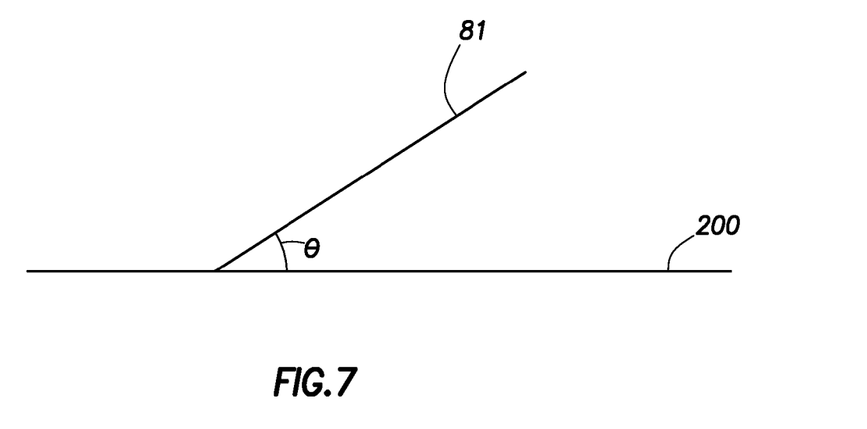
FIG. 7 illustrates a central axis of a container of the device being in a substantially horizontal position.

The device includes a container 20. The container 20 has a central axis 81 that spans the length of the container 20. To simulate a pipe in a horizontal position, the length of the container 20 is greater than the width and height of the container 20. Further, the central axis of the container is oriented in a substantially horizontal position during the duration of the testing. As used herein, the phrase "substantially horizontal" means in a position substantially parallel with respect to the surface of the Earth and wherein an angle of the central axis of the container and a plane of the Earth's surface is an angle whereby liquid in the container could flow out of the top, open end of the container. It is to be understood that the container does not have to be exactly parallel to the Earth's surface, but rather, the smallest angle θ between the central axis 81 of the container 20 and a plane of the Earth's surface 200 should not be less than 55°, wherein vertical is assigned 0° and the plane of the Earth's surface is assigned 90°. As such, as the central axis of the container moves from vertical towards horizontal, the smallest angle θ will increase from 0° towards a completely horizontal angle of 90°. FIG. 7 depicts an example of the angle θ between the central axis 81 of the container 20 and a plane of the Earth's surface 200. FIG. 7 is included for illustration purposes only and is not meant to show an actual angle of 55° or any specific value. While the teachings herein are most applicable to testing the amount of free fluid formed in a simulated wellbore, it is to be understood that the embodiments disclosed can be used when the container is in a vertical position as well. The angle θ for a container in a vertical position can be between 0° to approximately 55°.

The preferred arrangement of the container 20 is a cylinder having a circular cross-section to simulate a pipe. However, the container 20 may have other geometric cross-sectional shapes, including but not limited to, rectangular, pyramidal, oblique, oval, rhomboid, and combinations thereof. If the colloid is to be used in another structure other than a pipe, then the container may have a shape that represents the structure.

Optionally, the container 20 is preferably able to withstand different test parameters, e.g., temperature and/or pressure. For example, if the testing is to be performed at a temperature and/or pressure greater than ambient temperature and pressure, then the container should be capable of withstanding the testing temperature and/or pressure. As used herein, the term "withstanding" means that the structural integrity of the component (e.g., the container) is not compromised. For example, the container does not crack, break, or collapse.

The container 20 can be made from a variety of materials, including but not limited to those disclosed below. According to an embodiment, the material is selected from the group consisting of glass, plastic, polycarbonate plastic, thermoplastics, metal, metal alloys, and combinations thereof. In one embodiment, at least a portion of the container 20 is transparent so that measurements of the amount of free fluid may be performed. In another embodiment, at least two portions of the container 20 are transparent, and the portions are located near each end of the container 20, so that measurements of the amount of free fluid may be performed. In another embodiment, the entire container 20 is transparent. In a further embodiment, the entire container 20 is opaque, and measurements are made from another portion of the device, for example, the end cap(s) 21.

The device may include a diaphragm to allow for different pressures to be applied to the device.

In one embodiment, the container 20 is a cylinder that holds the known volume of the colloid. The dimensions of the container 20 can be any dimensions such that the entire known volume of the colloid is capable of being placed into the container. According to another embodiment, the container has a length to inner diameter ratio between 6:1 to 8:1.

The device may comprise at least one end cap 21. In one embodiment, the device comprises one removably attached end cap 21 located at one end of the container 20. The other end of the container may have a permanent cover or another permanent end cap 21 that is part of the container 20. In another embodiment, the device comprises two removably attached end caps 21 located at each end of the container 20.

The shape of the end cap 21 can be selected such that the container 20 is in a substantially horizontal position during the testing. By way of example, if the container 20 has a cross-sectional shape that is circular, then the end cap 21 can be square or rectangular in shape. The square or rectangular shape of the end cap 21 can be used to maintain the container 20 in the substantially horizontal position (i.e., the container does not roll off of a testing apparatus, such as a table). However, if the cross-sectional shape of the container 20 is square or rectangular, then the container 20 would not roll off of the testing apparatus and would be capable of being maintained in the substantially horizontal position during testing without the shape of the end cap being responsible for the testing position. For a cylindrical container, one side of the end cap 21 is preferably flat so as to support the container in the substantially horizontal position during testing.

Figure 1A:
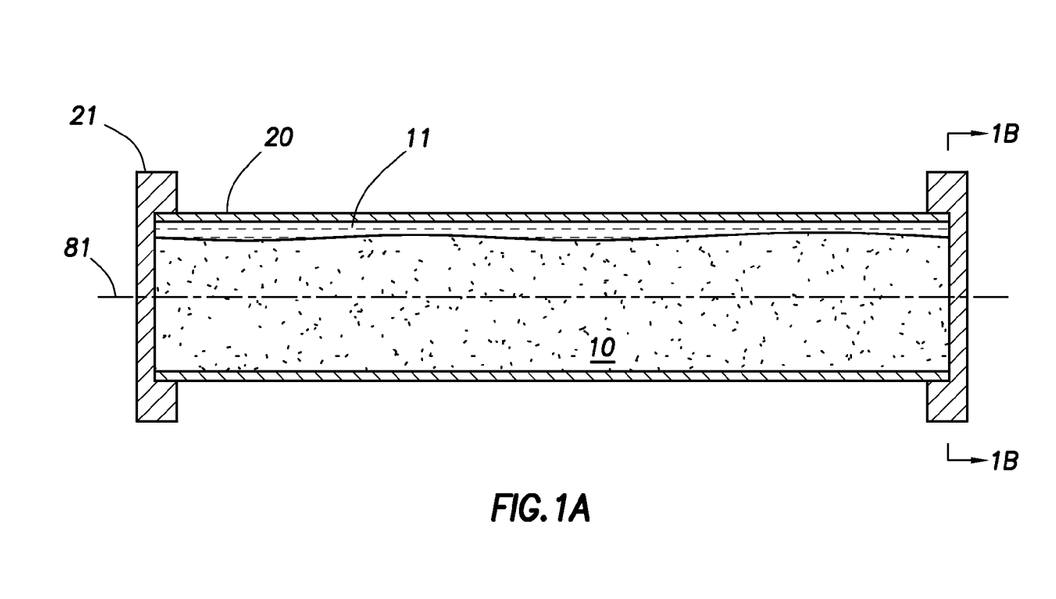
FIG. 1A depicts an example of an embodiment of a device for testing the amount of free fluid in a colloid.
Figure 1B:
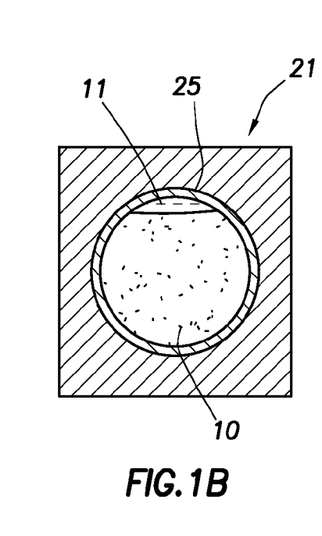
FIG. 1B is an end view of the device showing the end cap.

As can be seen in FIG. 1B, the end cap 21 can include a milled portion 25 that receives the container 20 and provides a seal to prevent the colloid or free fluid from independently exiting the container. The milled portion can be sized to fit the container. For example, the milled portion can match the inner and outer diameters of the container 20 described above. The depth of the mill may be selected such that the container is capable of fitting down into the end cap so a seal is created.

The end cap 21 can be made from the same material as the container 20 or a different material(s), disclosed above. The end cap should be able to withstand the same environmental conditions as the container 20. In one embodiment, at least a portion of the end cap 21 is transparent so that measurements of amount of free fluid may be performed. In another embodiment, at least one portion of the two end caps is transparent so that measurements of amount of free fluid may be performed at each end of the device. In another embodiment, the entire end cap 21 is transparent. In a further embodiment, the entire end cap 21 is opaque, and measurements are made from another portion of the device, e.g., the container 20.

Figure 4:
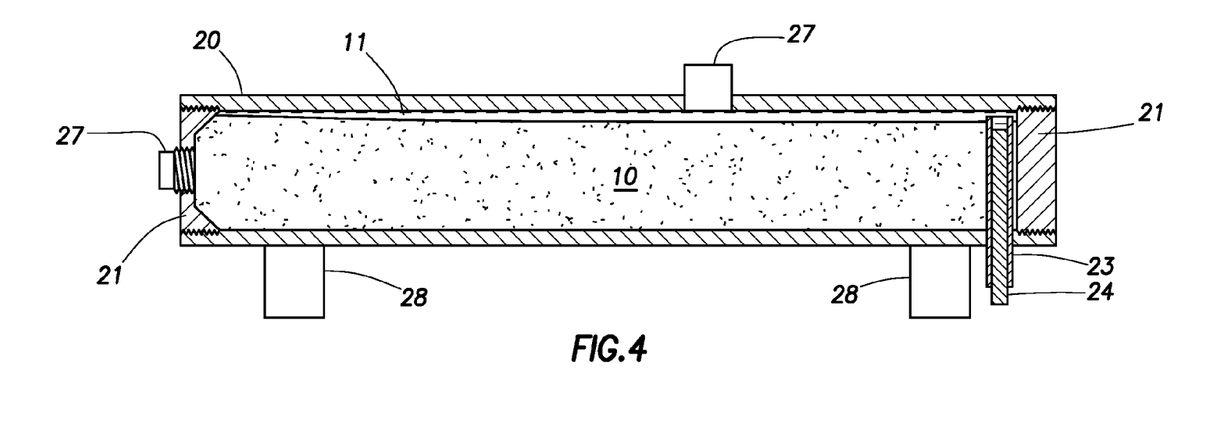
FIG. 4 depicts the device according to certain embodiments wherein the device further includes support members and optional fill ports.
Figure 5:
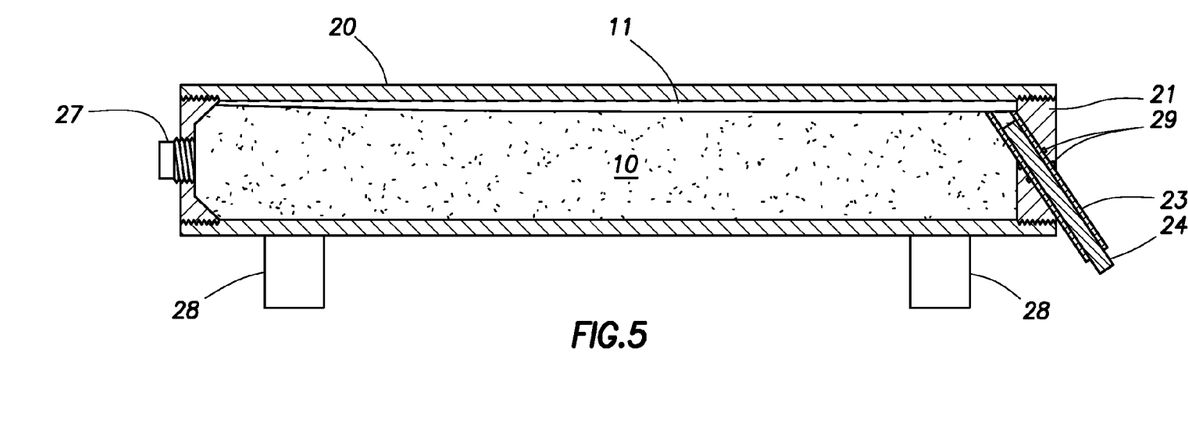
FIG. 5 depicts the plug tube of FIG. 2 according to another embodiment.

As shown in FIG. 1A, the device uses two end caps 21, and depending on the shape of the cross-section of the container, each end cap 21 also supports the device in a substantially horizontal position. As also shown in FIG. 1A, the end cap(s) can slidingly engage the container 20 such that a seal is created for containing the colloid and the free fluid. By contrast, and as shown in FIGS. 4 and 5, the end cap 21 can be threadedly connected to the container 20. For example, the end cap 21 can be screwed onto the container 20 to create the seal via threads on the end of the end cap and the end of the container. According to this embodiment, and as shown in FIGS. 4 and 5, the end cap can be circular in shape. Therefore, in order for the container 20 to be in a substantially horizontal position during testing, the device can further comprise one or more support members 28. The support members 28 can include a flat surface so as to prevent a cylindrical container 20 from rolling off of a testing apparatus and be maintained in the substantially horizontal position during testing.

As shown in FIG. 7, the container 20 can be maintained in a substantially horizontal position during testing. As stated above regarding substantially horizontal, the smallest angle $\theta$ of the central axis 81 and the plane of the Earth's surface 200 is greater than 55°. The end cap 21 and/or the support members 28 may be sized to form a particular angle. For example, the end caps can have equal sizes such that $\theta$ is 90°. For angles between 55° and 90°, the end caps may have different dimensions. For example, the height of one end cap can be different from the height of the other end cap. The difference in height can be used to form the angle $\theta$, for example, if the container is placed on a table that is parallel to the plane of the Earth's surface. Moreover, the support members 28 can have the same or different heights. Alternatively, one of the end caps or supports may have adjustable leg(s) to raise one side of the container to a particular height, thereby forming the particular angle. For adjustable end caps or supports, an angularly adjustable bubble sight level may be used to ensure that the container is held at a particular angle. The angle can also be made via the use of other components not shown in the drawings, for example, laboratory jacks.

According to another embodiment, a method for testing the amount of free fluid in a colloid comprises: filling a container with a known amount of the colloid; maintaining the container with the colloid for a period of time in a substantially horizontal position; optically determining the height of free fluid in the container after the period of time has elapsed; and using a formula to determine the volume of the free fluid.

According to an embodiment, the amount of free fluid can be measured on the container itself. For this embodiment, the container 20 can have a desired number of graduated lines (not shown) at one or more locations to allow for optically measuring the amount of the free fluid. The number of graduated lines and their spacing can be varied such that a known volume of fluid separates each of the graduated lines. For example, the difference in volume between each graduated line can be 5 milliliters (mL) or 1 mL. The volume of free fluid can then be optically determined by looking at the graduated lines.

Optionally, the end cap(s) 21 can have a desired number of graduated lines (not shown) at one or more locations to allow for optically measuring the amount of the free fluid. The specifics for the graduated lines can be similar to the graduated lines on the container, discussed above.

The following is one example for using the device of FIG. 1A. One end cap 21 can be secured to an open end of the container 20, and the device can be turned substantially vertical with the end cap acting as a base for the container. The container can then be filled with the known volume of the colloid 10 via the other open end of the container. Another end cap can then be secured onto the container, and the container can be maneuvered to the substantially horizontal position. After the requisite period of time has passed, the amount of free fluid 11 can be determined via the graduated lines on the device. Alternatively, a height measuring device, such as calipers, can be used to measure the height of the free fluid 11. The height of the free fluid can then be used to calculate the exact volume of free fluid in the container.

Figure 1C:
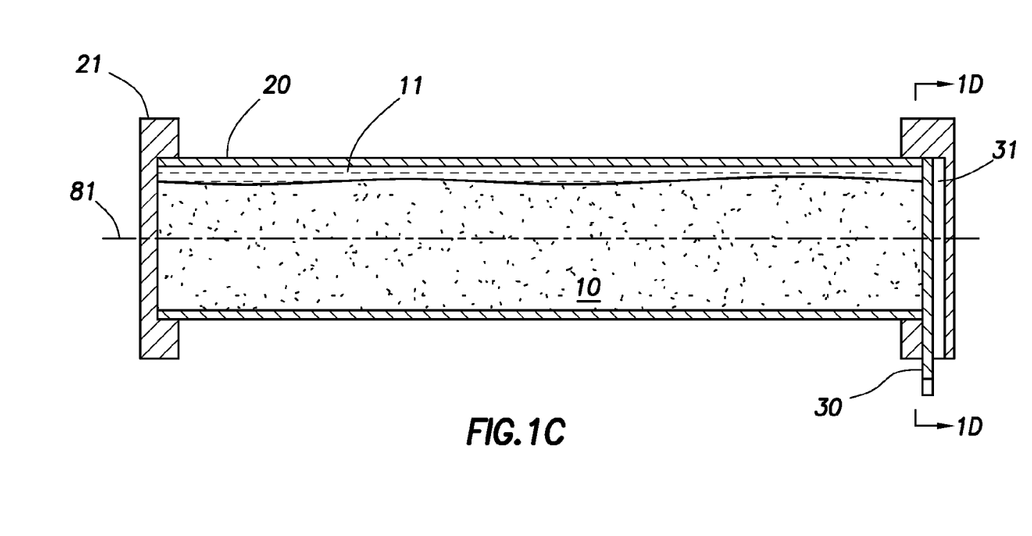
FIG. 1C depicts an example of another embodiment of the device including a sliding plate.
Figure 1D:
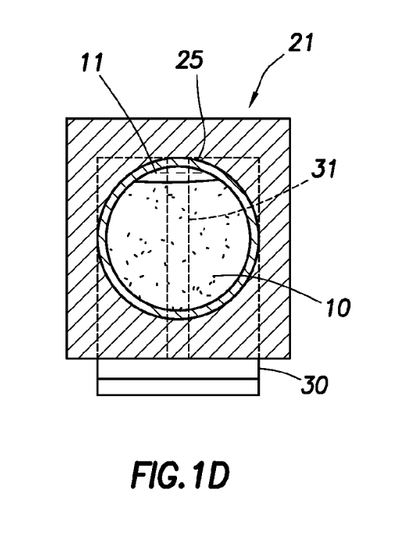
FIG. 1D is an end view of the device showing the end cap of FIG. 1C.

The following is another example for using the device of FIG. 1A. As can be seen in FIGS. 1C and 1D, at least one end cap 21 can further comprise a sliding plate 30. The sliding plate 30 can be positioned immediately adjacent to an end of the container 20. The end cap 21 can be attached to the container 20 by pressing the end cap onto the end of the container. The sliding plate 30 functions as a seal such that the colloid 10 and free fluid 11 remain in the container for the desired period of time. The end cap 21 can also contain a fluid passageway 31. After the desired period of time has elapsed, the sliding plate 30 can be pulled downward to expose the free fluid 11 to the fluid passageway 31. The free fluid 11 can then flow through the fluid passageway 31 into a separate measuring container for determining the amount of free fluid. The sliding plate 30 can be pulled downward as far as needed to allow all of the free fluid 11 to flow into the separate container. In this manner, it is very easy to remove the free fluid 11 from the container 20. The sliding plate 30 can be made from a variety of materials and can include a lubricant to help aid in movement of the plate downwards. The sliding plate 30 can also include a locking mechanism (not shown) to prevent premature downward movement of the plate. One or more support members 28 are preferably used for this embodiment as the sliding plate 30 will need clearance for the downward movement.

The following equations are some examples for calculating the volume of the free fluid. Note that other formulas may be used.

$$h_{avg} = \frac{h_1 + h_2}{2} \qquad \text{Equation 1}$$

havg Average height of free fluid [in]
h1 Height of free fluid at one location [in]
h2 Height of free fluid at second location [in]

Equation 1 determines an average height of the free fluid in the container 20. In one embodiment, the locations for $h_1$ and $h_2$ may be the end caps. In another embodiment, the locations may be at distal positions on the container. Note that additional measurements may be used to form the average height. For example, three or four height measurements may be taken along the length of the container. To determine the average height, the sum of each measurement is divided by the total number of measurements. Further note, that one measurement may be taken at one location, e.g., at the center of the container 20. In this case, that measurement is used as the average height.

$$V_1 = C \cdot (L - d_1 - d_2) \cdot \frac{R^2}{2} \cdot \left[ 2 \cdot \cos^{-1}\left(\frac{R - h_{avg}}{R}\right) - \sin\left(2 \cdot \cos^{-1}\left(\frac{R - h_{avg}}{R}\right)\right) \right]$$

Equation 2

V1 Volume of free fluid when havg<R [mL]
C Conversion factor=16.3871 [mL/in³]
d1 Depth of milled portion 25 in first end cap 21 [in]
d2 Depth of milled portion 25 in second end cap 21 [in]
L Full length of the container 20 [in]
R Inner radius of container 20 [in]

$$V_2 = \pi \cdot R^2 - C \cdot (L - d_1 - d_2) \cdot \frac{R^2}{2} \cdot \left[ 2 \cdot \cos^{-1}\left(\frac{h_{avg} - R}{R}\right) - \sin\left(2 \cdot \cos^{-1}\left(\frac{h_{avg} - R}{R}\right)\right) \right]$$

Equation 3

V2 Volume of free fluid when havg>R [mL]
C Conversion factor=16.3871 [mL/in3]
d1 Depth of milled portion 25 in end cap 21 [in]
d2 Depth of milled portion 25 in end cap 21 [in]
L Full length of the container 20 [in]
R Inner radius of container 20 [in]

Equation 2 would be used when the height of the free fluid is smaller than the radius of the container. In other words, there is more colloid than free fluid. Equation 3 would be used when the height of the free fluid is greater than the radius of the container. In other words there is more free fluid than colloid. When $h_{avg}=R$, then either Equation 2 or 3 can be used. Note that these formulas are for use with the units as shown. Equivalent formulas may be used with different units, wherein additional conversion factor(s) would be inserted as needed.

Once the volume of free fluid is determined (e.g., via graduated lines, the equations above, or other methods described below), the volume fraction φ of the free fluid to the colloid is calculated using the following equation and expressed as a percentage:

$$\varphi = \frac{Vf}{Vs} * 100$$

where Vf is the volume of free fluid and Vs is the known volume of the colloid.

According to a further embodiment, a method for testing the amount of free fluid in a colloid comprises: filling a container with a known amount of the colloid; maintaining the container with the colloid for a period of time in a substantially horizontal position; removing a plug from a plug tube that is operationally connected to the container after the period of time has elapsed, wherein an end of the plug tube is positioned in at least a portion of the free fluid; and draining the free fluid from the container into a measurement device.

Figure 2:
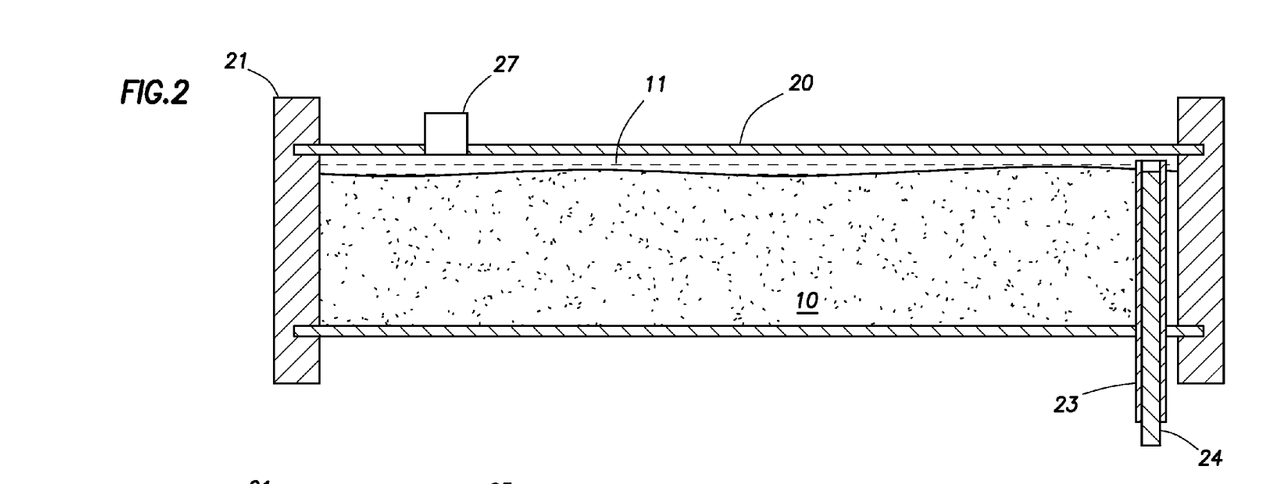
FIG. 2 depicts an alternative embodiment for the device of FIGS. 1A and 1B wherein a plug tube is located within an end cap.

FIG. 2 depicts an example of another embodiment of a device for testing the amount of free fluid in a colloid. This device is similar to that of FIG. 1A and includes a plug tube 23 with a plug 24. The plug tube 23 can be slidably fitted into the container 20 and has a length greater than the diameter of the container. The plug 24 can be removably fitted into the plug tube 23. The plug 24 extends the length of the plug tube 23 and prevents the colloid from flowing into the plug tube. Optionally, the container may use a fill port 27 to fill the container with the colloid as opposed to filling the container from an open end of the container. This would allow the end caps to be fixed to the container 20 prior to filling. The plug 24 can be impermeable to fluids. The plug 24 may comprise permeable materials that are coated with impermeable materials, e.g., grease.

In one embodiment, the support member 28 is positioned proximate to the center of the length of the container along the external surface of the container (not shown). In another embodiment, two support members are positioned proximate to the first and second ends of the first container and adjacent to an external surface of the cylinder. In a further embodiment, more than three or more support members are located along the length of the container (not shown).

According to these embodiments shown in FIGS. 2-6A, the free fluid 11 can be drained from the container 20 into a separate measurement device, e.g., a graduated cylinder. This would allow for a measurement of the actual volume of the free fluid from the container. Alternately, the volume of free fluid can be calculated by weighing the drained free fluid and dividing the weight by the density of the free fluid. The volume of free fluid can then be used to calculate the volume fraction of the free fluid in the colloid.

The free fluid can be drained by first removing the plug 24 from the plug tube 23 and allowing the free fluid to drain into the measurement device. The plug tube can be moved downward until the opening of the plug tube is at the boundary of the free fluid and the remaining colloid. This allows all (or substantially all) of the free fluid to be drained from the container 20 without draining the colloid.

Figure 3A:
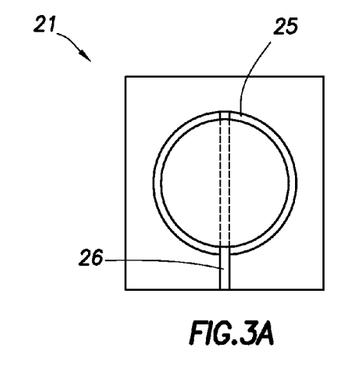
FIGS. 3A and 3B are end views and side views, respectively, of the end cap according to certain embodiments wherein the end cap contains milled portions.
Figure 3B:
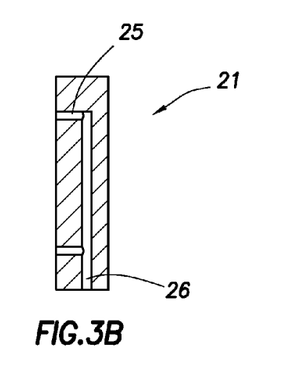

FIGS. 3A and 3B depict the plug tube 23 according to another embodiment. FIG. 3A is an end view of the end cap and FIG. 3B is a side view of the end cap according to this other embodiment. This device is similar to that of FIG. 2 except the plug tube 23 is located within the end cap 21. This embodiment would operate similar to that of FIG. 2 for draining the free fluid from the container. As can be seen in FIG. 3B, the end cap 21 can further include a milled portion 26 for receiving the plug tube 23. Of course, the end cap 21 can also include the milled portion 25 for receiving the container 20.

As shown in FIG. 4, the fill port 27 can be located along the length of the container 20 or at one end of the container 20. In this manner, the container 20 can be filled with the known volume of the colloid when the container 20 is in the substantially horizontal or substantially vertical position.

FIG. 5 depicts the plug tube 23 positioned within the end cap 21 instead of within the container 20. According to this embodiment, the device can further include one or more seals 29 for creating a seal around the plug tube 23 in the end cap 21. The seals 29 can be any component that is capable of creating a seal around the plug tube 23 such that the colloid and free fluid do not flow out of the container 20, but rather, the free fluid can be drained from the container 20 solely via the plug tube 23. The seals 29 can be for example, O-rings. The plug tube 23 may not be slidingly connected to the container, but can be permanently attached to the container 20 within the end cap 21. Note with this arrangement, if the free fluid extends below the opening in the end cap, then some of the free fluid may not be capable of being drained from the container. The plug tube 23 can be angled in the end cap 21 such that the free fluid drained from the plug tube 23 can be easily collected. If the plug tube 23 is located within the container 20, then the height of the end cap 21, support member 28, and plug tube 23 can be selected such that the drained free fluid is easily capable of being collected. For example, the height of the end cap and/or support member can be selected such that a collection device can be placed underneath the plug tube for collecting the drained free fluid. By way of another example, the plug tube 23 can also include a flexible portion at the end of the plug tube where the free fluid will drain out. In this manner, the flexible end of the plug tube can be bent after removal of the plug 24 such that the free fluid draining out of the container 20 can flow into a collection device.

Figure 6A:
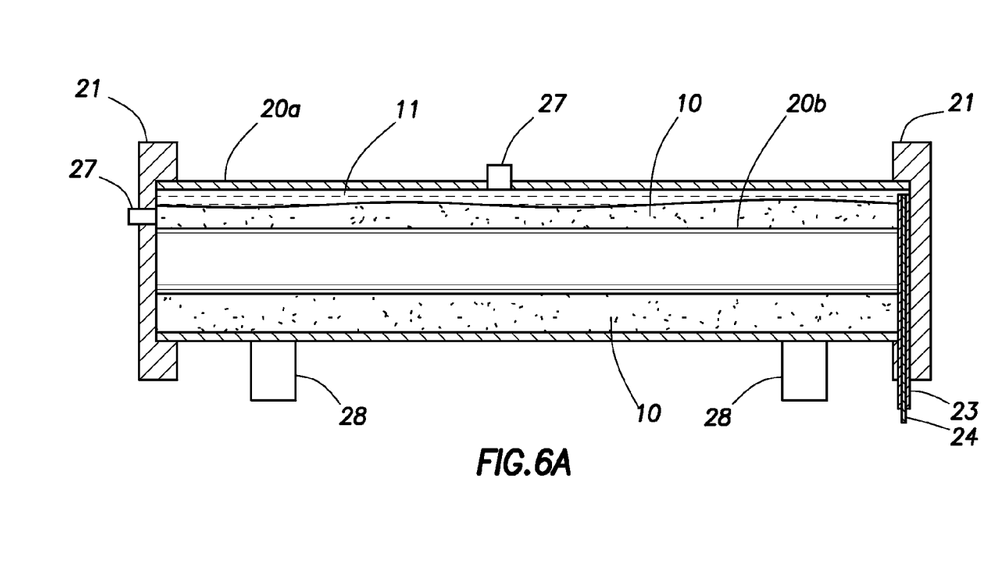
FIGS. 6A-6C depict the device according to another embodiment wherein the device includes a first and second container.
Figure 6B:
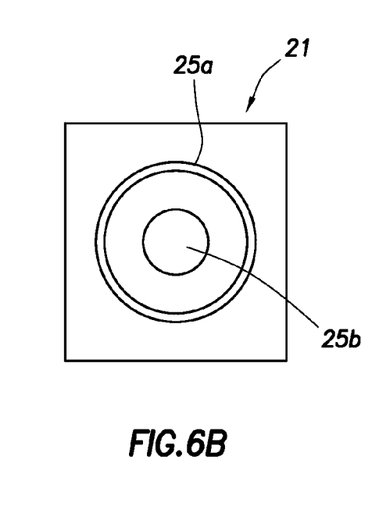
Figure 6C:
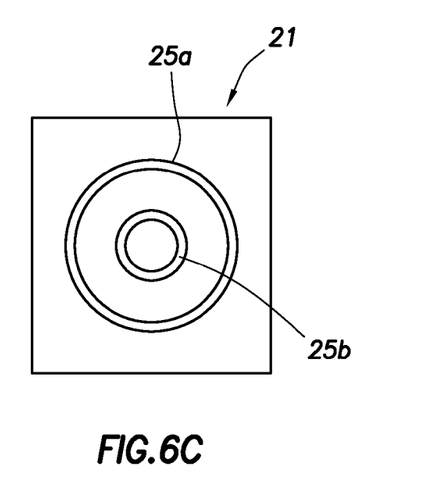

FIGS. 6A-6C depict another example of a device for testing the amount of free fluid in a colloid. This device includes a first container 20a and a second container 20b. According to this embodiment, the colloid 10 is filled into the space between the inner diameter of the first container 20a and the outer diameter of the second container 20b. This embodiment may be useful when simulating a cementing operation in an annulus between the outside of a casing and the inside of a wall of a wellbore or another tubing. The second container 20b can have a variety of cross-sectional shapes (discussed above). The second container 20b can be hollow or solid. FIG. 6B depicts an example of an end cap 21 used when the second container 20b is solid. As can be seen in FIG. 6B, the end cap 21 can include the milled portion 25a for receiving the first container 20a and a milled portion 25b for receiving the second container 20b. Although not shown in FIGS. 6B and 6C, the end cap 21 can also include the milled portion 26 for receiving or holding the plug tube 23. FIG. 6C depicts an example of an end cap 21 used when the second container 20b is hollow. As can be seen in FIG. 6C, the end cap 21 can include the milled portion 25a for receiving the first container 20a and a milled portion 25b for receiving the second container 20b. One end of the plug tube can be located at a boundary between the end cap 21 and the containers 20a, 20b. Alternatively, the first container 20a can include graduated lines for visually determining the volume of free fluid or height measurements can also be used to determine the average height of the free fluid.

The embodiments disclosing the use of a plug tube may be more useful to liquid continuous phase free fluids, such as solutions, emulsions, or invert emulsions. The plug tube may not be suited for use when the free fluid is a mist or foam in which case graduated lines or height measurements via calipers, for example, can be used to determine the amount of free fluid in the colloid.

Note that the discussion pertaining to a cement composition is used by way of example only, and the devices and methods discussed herein can be used with other substances in addition to a cement composition. Moreover, testing of the amount of free fluid can also be performed in a vertical position (i.e., where the angle θ is between 0° and 55° with reference to FIG. 7, discussed above).

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is, therefore, evident that the particular illustrative embodiments disclosed above may be altered or modified and all such variations are considered within the scope and spirit of the present invention. While compositions and methods are described in terms of "comprising," "containing," or "including" various components or steps, the compositions and methods also can "consist essentially of" or "consist of" the various components and steps. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an", as used in the claims, are defined herein to mean one or more than one of the element that it introduces. If there is any conflict in the usages of a word or term in this specification and one or more patent(s) or other documents that may be incorporated herein by reference, the definitions that are consistent with this specification should be adopted.

What is claimed is:

1. A device for testing the amount of free fluid in a colloid comprising:
    a first container, wherein the first container has a central axis that spans the length of the first container, wherein the length of the first container is greater than the width and height of the first container, wherein the first container has a cross-sectional shape selected from the group consisting of rectangular, pyramidal, oblique, oval, rhomboid, wherein the central axis of the first container is oriented in a substantially horizontal position during the testing, wherein the first container comprises at least two endcaps capable of being coupled to the first container, wherein at least one of the at least two endcaps comprises a sliding plate, wherein the sliding plate forms a seal with the first container, wherein the endcap further comprises a fluid passageway adjacent to the sliding plate, wherein the sliding plate is movable such that the sliding plate may be adjusted to allow fluid flow into the fluid passageway of a fluid disposed in the first container while the at least one endcap comprising the sliding plate is coupled to the first container.

2. The device according to claim 1, wherein the colloid is a slurry.

3. The device according to claim 2, wherein the slurry is a cement composition.

4. The device according to claim 1, wherein at least a portion of the first container is transparent.

5. The device according to claim 1, wherein the first container is made from a material selected from the group consisting of glass, plastic, polycarbonate plastic, thermoplastics, metal, metal alloys, and combinations thereof.

6. The device according to claim 1, wherein the first container comprises a plurality of graduated lines.

7. The device according to claim 6, wherein the plurality of graduated lines are used to determine the total volume of the free fluid.

8. The device according to claim 1, wherein a first end cap is permanently or removably attached to a first end of the first container, and wherein a second end cap is permanently or removably attached to a second end of the first container.

9. The device according to claim 1, wherein each end cap includes a milled portion that receives the ends of the container.

10. The device according to claim 1, wherein at least one of the end caps is transparent.

11. The device according to claim 10, wherein the end cap that is transparent further comprises graduated lines.

12. The device according to claim 1, further comprising at least one support.

13. The device according to claim 1, further comprising a moveable plug tube that is inserted into a portion of the container, and a moveable plug that is inserted into the moveable plug tube.

14. The device of claim 1, further comprising a moveable plug tube that is inserted into a portion of one of the end caps, and a moveable plug that is inserted into the moveable plug tube.

15. The device according to claim 1, further comprising a second container that is located with the first container, whereby the colloid fills the space between the inner diameter of the first container and the outer diameter of the second container.

* * * * *